(12) United States Patent
Foster

(10) Patent No.: US 9,173,565 B2
(45) Date of Patent: Nov. 3, 2015

(54) AUTOMATED VISION SCREENING APPARATUS AND METHOD

(75) Inventor: Bart Foster, Suwanee, GA (US)

(73) Assignee: Pursuant Health, Inc., Duluth, GA (US)

( * ) Notice: Subject to any disclaimer, the term of this patent is extended or adjusted under 35 U.S.C. 154(b) by 0 days.

(21) Appl. No.: 12/545,405

(22) Filed: Aug. 21, 2009

(65) Prior Publication Data
US 2009/0310084 A1 Dec. 17, 2009

Related U.S. Application Data

(62) Division of application No. 10/985,524, filed on Nov. 10, 2004, now Pat. No. 7,614,747.

(60) Provisional application No. 60/591,670, filed on Jul. 28, 2004.

(51) Int. Cl.
| | | |
|---|---|---|
| A61B 3/02 | (2006.01) | |
| A61B 3/10 | (2006.01) | |
| A61B 3/18 | (2006.01) | |
| A61B 3/06 | (2006.01) | |
| A61B 5/117 | (2006.01) | |

(52) U.S. Cl.
CPC ... *A61B 3/18* (2013.01); *A61B 3/06* (2013.01); *A61B 5/117* (2013.01)

(58) Field of Classification Search
USPC ......... 351/246, 205, 211, 222, 223, 200, 202, 351/203, 206, 209, 224, 239, 245
See application file for complete search history.

(56) References Cited

U.S. PATENT DOCUMENTS

| | | | | |
|---|---|---|---|---|
| 4,105,302 | A * | 8/1978 | Tate, Jr. | 351/210 |
| 4,869,589 | A * | 9/1989 | Blair et al. | 351/243 |
| 5,914,772 | A | 6/1999 | Dyer | |
| 5,929,972 | A | 7/1999 | Hutchinson | |
| 6,422,700 | B2 * | 7/2002 | Ohyagi | 351/239 |
| 6,450,643 | B1 | 9/2002 | Wilson | |
| 6,540,643 | B2 | 4/2003 | Ohtsuka | |
| 6,592,223 | B1 | 7/2003 | Stern et al. | |

(Continued)

FOREIGN PATENT DOCUMENTS

| | | | | |
|---|---|---|---|---|
| JP | 11-137519 | * 11/1997 | | A61B 3/028 |
| JP | 2001-286442 | 10/2001 | | |

(Continued)

OTHER PUBLICATIONS

Solomon, Bruce, "Vision Centers by Panaseca" Jan. 27, 2005, pp. 1-7.

(Continued)

*Primary Examiner* — Stephone B Allen
*Assistant Examiner* — Brandi Thomas
(74) *Attorney, Agent, or Firm* — Womble Carlyle Sandridge & Rice LLP

(57) ABSTRACT

This invention is related to a self-service vision screening kiosk that allows individuals to screen their eyesight without assistance. The device includes subjective and/or objective tests via an interactive video and software program that measures visual acuity and contrast sensitivity. The invention is designed to provide a report with test results. The device and method may also provide a means for making referrals, scheduling appointments, ordering lenses, dispensing lenses and/or forwarding prescriptions to eye care professionals or lens manufacturers.

26 Claims, 4 Drawing Sheets

(56) References Cited

U.S. PATENT DOCUMENTS

| | | |
|---|---|---|
| 6,594,607 B2 | 7/2003 | Lavery |
| 6,687,389 B2 | 2/2004 | McCartney et al. |
| 6,726,633 B2 | 4/2004 | Kitagawa |
| 6,761,453 B2 | 7/2004 | Wilson |
| 6,899,428 B2 | 5/2005 | Mihashi |
| 7,233,312 B2 | 6/2007 | Stern et al. |
| 7,350,921 B2 | 4/2008 | Ridings |
| 7,437,344 B2 | 10/2008 | Peyrelevade |
| 8,182,091 B2 | 5/2012 | Foster |
| 2001/0025226 A1 | 9/2001 | Lavery |
| 2002/0021411 A1 | 2/2002 | Wilson |
| 2002/0080329 A1 | 6/2002 | Kasahara |
| 2003/0020877 A1 | 1/2003 | Marrou |
| 2003/0058404 A1 | 3/2003 | Thorn et al. |
| 2003/0065636 A1 | 4/2003 | Peyrelevade |
| 2003/0117580 A1 | 6/2003 | Franz et al. |
| 2003/0208190 A1 | 11/2003 | Roberts et al. |
| 2004/0076942 A1* | 4/2004 | O'Neil et al. .......... 434/350 |
| 2004/0141152 A1* | 7/2004 | Marino et al. .......... 351/222 |
| 2005/0273359 A1 | 12/2005 | Young |
| 2009/0228304 A1 | 9/2009 | Ciarniello et al. |
| 2009/0241177 A1 | 9/2009 | Bluth |
| 2011/0299034 A1 | 12/2011 | Walsh |

FOREIGN PATENT DOCUMENTS

| | | |
|---|---|---|
| JP | 2002-10977 | 1/2002 |
| JP | 2002-78679 | 3/2002 |
| JP | 2002-78681 | 3/2002 |
| JP | 2002-83156 | 3/2002 |
| JP | 2002-238858 | 8/2002 |
| JP | 2003-57021 | 2/2003 |
| JP | 2003-57038 | 2/2003 |
| JP | 2003-75785 | 3/2003 |
| JP | 2003-228623 | 8/2003 |
| JP | 2004-33637 | 2/2004 |
| JP | 2004-34893 | 2/2004 |
| WO | WO 03/007392 | 11/2003 |
| WO | 2006010611 A1 | 2/2006 |
| WO | 2006029048 A2 | 3/2006 |

OTHER PUBLICATIONS

Panaseca, Inc., "Welcome to the Eye Advisor: Your Self-Care Eye Health Information Center," Copyright 2003, pp. A1-A18.
Panaseca, Inc., "Panaseca Office Pro", [Date Unknown], pp. B1-B4.
Office Action issued r in Japanese Application No. 2007-023014, mailed Jan. 5, 2011.
English language translation of Office Action issued in Japanese Application No. 2007-523014, mailed Jan. 5, 2011.
English language abstract of JP 2002-83156, published Mar. 22, 2002.
Machine English language translation of JP 2002-83156, published Mar. 22, 2002.
English language abstract of JP 2002-78681, published Mar. 19, 2002.
Machine English language translation of JP 2002-78681, published Mar. 19, 2002.
English language abstract 2002 of JP 2002-78679, published Mar. 19, 2002.
Machine English language translation of JP 2002-78679, published Mar. 19, 2002.
English language abstract of JP 2003-228623, published Aug. 15, 2003.
Machine English language translation of JP 2003-228623, published Aug. 15, 2003.
English language abstract of JP 2002-238858, published Aug. 27, 2002.
Machine English language translation of JP 2002-238858, published Aug. 27, 2002.
English language abstract of JP 2004-34893, published Feb. 5, 2004.
Machine English language translation of JP 2004-34893, published Feb. 5, 2004.
English language abstract of JP 2004-33637, published Feb. 5, 2004.
Machine English language translation of JP 2004-33637, published Feb. 5, 2004.
English language abstract of JP 2003-57038, published Feb. 26, 2003.
Machine English language translation of JP 2003-57038, published Feb. 26, 2003.
English language abstract of JP 2003-57021, published Feb. 26, 2003.
Machine English language translation of JP 2003-57021, published Feb. 26, 2003.
English language abstract of JP 2003-75785, published Mar. 12, 2003.
Machine English language translation of JP 2003-75785, published Mar. 12, 2003.
English language abstract of JP 2001-286442, published Oct. 16, 2001.
Machine English language translation of JP 2001-286442, published Oct. 16, 2001.
English language abstract of JP 2002-10977, published Jan. 15, 2002.
Machine English language translation of JP 2002-10977, published Jan. 15, 2002.
U.S. Appl. No. 10/985,524.
U.S. Appl. No. 09/783,449.
International Search Report issued in International Application No. PCT/EP2005/008158, mailed Nov. 28, 2005.
Written Opinion issued in International Application No. PCT/EP2005/008158, mailed Nov. 28, 2005.
Office Action issued in EP 05778082.7, mailed Sep. 16, 2009.
Office Action issued in EP 05778082.7, mailed Feb. 2, 2010.
Office Action issued in EP 05778082.7, mailed Jun. 2, 2010.
Office Action issued in EP 05778082.7, mailed Jan. 10, 2011.
U.S. Appl. No. 12/364,925.
U.S. Appl. No. 13/929,230.
U.S. Appl. No. 13/440,804.
U.S. Appl. No. 13/969,429.
U.S. Appl. No. 14/252,171.

* cited by examiner

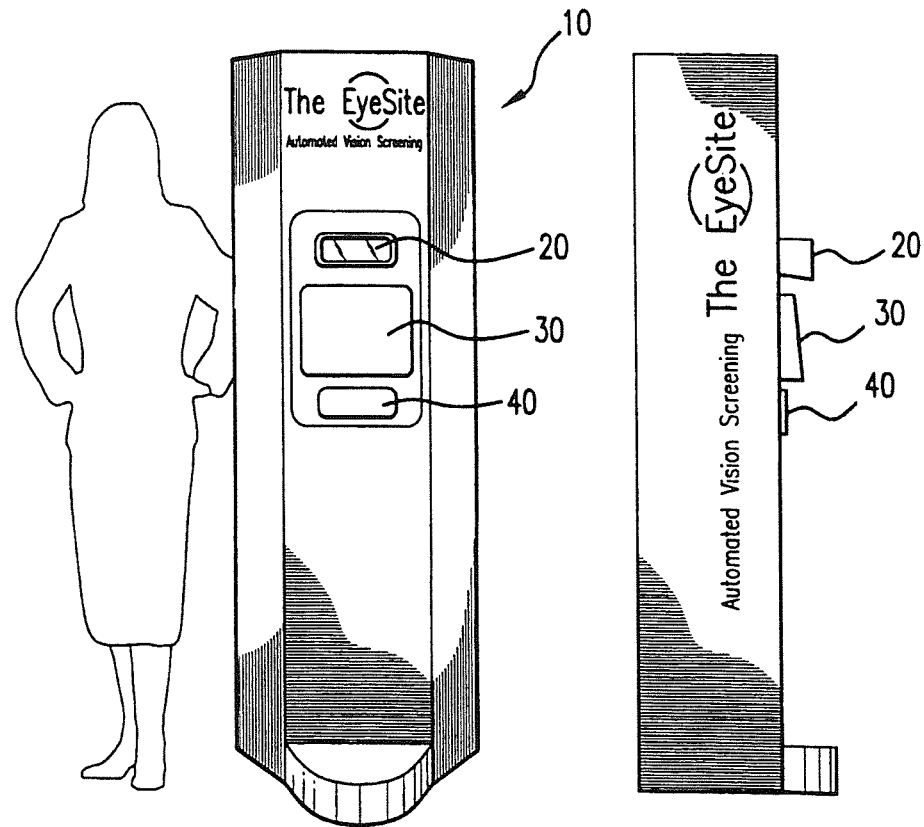
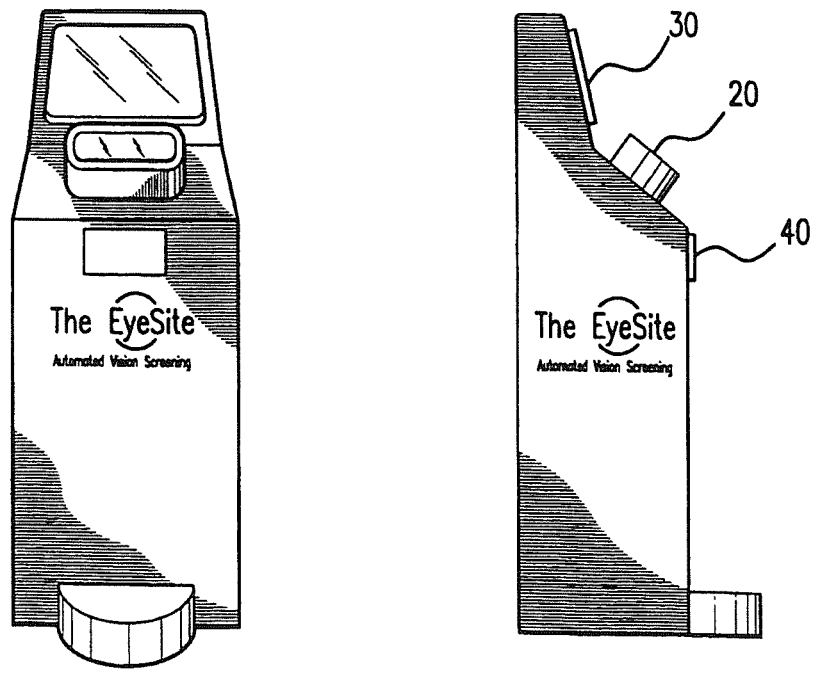
FIG. 1A  FIG. 1B  FIG. 1C  FIG. 1D

Thank you for using EyeSite automated vision screening

EyeSite

This vision screening is only an estimate of your current sight.
It can indicate that you need to get an eye exam, but
it does not serve as a substitute for a comprehensive eye exam.

Your Distance Vision is:

| LEFT EYE 20/10 | RIGHT EYE 20/20 |

LEFT EYE / RIGHT EYE
What this means:

20/20 Normal Vision. It means a person can clearly see an object from 20 feet that the average person with normal vision can see at the same distance.

20/30 You can see at 20 feet what the average person with normal vision can see at 30 feet.

20/40 You can see at 20 feet what the average person with normal vision can see at 40 feet.

20/60 You can see at 20 feet what the average person can see at 60 feet.

To have your eyes properly evaluated, please make an appointment with a qualified optician for a comprehensive eye examination.

A comprehensive eye examination will involve careful testing of all aspects of your vision. Based upon the results of your exam, the eye care professional will then recommend a treatment plan for your individual needs. Remember, only an eye care professional can provide a comprehensive eye exam – most family physicians and pediatricians are not fully trained to do this, and studies have shown that they can miss important vision problems that require treatment.

Treatment plans can include glasses or contact lenses for blur, eye exercises or surgery for muscle problems, medical treatment for eye disease or simply a recommendation that you have your eyes examined again in another couple of years.

No matter who you are, regular eye exams are important for seeing more clearly, learning more easily and preserving your vision for life.

---

Present this voucher to one of the
following opticians near you and receive
$5 OFF
a complete eye examination XYZ Opticians, 104 St. Cross Road, Winchester
ABC Optical, 200 Mead Road, Winchester
Spectacles, 123 St. Cross Road, Winchester
*Offer Expires: 10/31/2004

FREE

NIGHT & DAY Trial
plus $20 OFF your first purchase
Please present this voucher to your
local optician.
*Offer Expires 10/31/2004

FIG.2

AUTOMATED VISION SCREENING APPARATUS AND METHOD

CROSS-REFERENCE TO RELATED APPLICATIONS

This application is a divisional of U.S. Non-Provisional patent application Ser. No. 10/985,524 filed Nov. 10, 2004, which claims the benefit under 35 USC §119 (e) of U.S. Provisional Patent Application Ser. No. 60/591,670 filed Jul. 28, 2004, both of which are hereby incorporated by reference in their entireties.

FIELD OF THE INVENTION

This invention is related to an automatic self-service vision screening kiosk and method that allows individuals to screen their eyesight without assistance. The device includes subjective and/or objective tests via an interactive video and software program that measures visual acuity and contrast sensitivity. The invention is designed to provide a report with test results. The device and method may also provide a means for making referrals, scheduling appointments, ordering lenses, dispensing lenses, and/or forwarding prescriptions to eye care professionals or lens manufacturers.

BACKGROUND

An estimated 164 million Americans require some form of vision correction. In 1999, only about 52 percent of persons needing vision correction purchased eyewear, leaving 48 percent, who purchased nothing.

The American Optometric Association recommends that a patient visit an optometrist every 1-2 years because eyesight can deteriorate slowly, making self-diagnosis difficult. Less than thirty percent of Americans that are age 40 and over realize the importance of regular eye exams. Two major reasons why consumers fail to visit their optometrist regularly are based upon convenience and belief that their vision remains static.

Additionally, some sectors of the general population are unable to participate in a typical exam performed in doctors' offices. For example, some consumers have special needs and may not comprehend the Snellen test. Other consumers, such as very young children may not be able to differentiate letters, numbers or other shapes used to diagnose vision defects. Other consumers may fear the expense of a lengthy eye exam in countries that require an exam for a vision correction prescription. Still consumers may experience a language barrier that makes a Snellen or refractive exam difficult or impossible.

Some countries do not require prescriptions for corrective lenses; however, individuals who do not know their sphere and cylinder corrections cannot accurately determine which lenses to order. Additionally, in some countries, eye care professionals may not be accessible to all individuals. In these countries, some individuals requiring vision correction may not have access to 1) methods to indicate the type and power of vision correction needed and 2) methods to obtain vision correction.

SUMMARY OF THE INVENTION

The present invention seeks to solve the problems listed herein by providing a device and method for measuring and reporting visual acuity at user convenience. The present invention also seeks to provide a means for a user to manage his or her optical health by providing referrals to eye care professionals and corrective lens producers. The invention may also provide a means for electronic communication between a user, practitioner and/or a corrective lens supplier/producer and/or eye care professional. The present invention may also provide an interactive eye care makeover that allows a user to view him/herself with varying types of vision correction.

In one embodiment, the invention comprises a method for screening vision without assistance at a kiosk that includes the steps of requesting user information, performing visual acuity tests, and reporting visual acuity results. In one embodiment objective visual acuity tests are performed by an automated adaptive optic phoropter, a badal optometer, a corneal topographer, a tonomer, a wavefront sensor, and/or a Fundus camera. In another embodiment, subjective tests, such as a Snellen test or a Landolt C test are automated. In another embodiment, other tests, such as tests for glaucoma or color vision deficiency may be performed. The invention preferably determines subjectively or objectively based visual acuity at distance and near. In another embodiment, the patient's refractive error, including sphere, cylinder, and cylinder axis are provided. In still another embodiment the results are reported at the user kiosk or via the internet to a third party, which may include an eye care professional, a lens supplier, a lens distributor, a lens manufacturer and/or a web database. In one embodiment, the results may be reported via a SmartCard®.

In another embodiment, the invention may be used to provide referrals to or appointments with a eye care professional. In an alternative embodiment, the present invention may perform a virtual eye care makeover. In still another embodiment, the invention may dispense plano lenses. In one embodiment, the invention requests payment from a consumer.

The invention also provides a user kiosk for automatic visual acuity screening that includes vision test instrumentation, at least one microprocessor, a shell, a WAN/LAN connection, a communication means, and/or a reporting means. The invention may also include a credit and coin payment device, remote management software, a digital camera, and/or Customer Relationship Management System (CRM). In one embodiment the communication means may be a visual communication means, which may be a touch screen or a keyboard. In another embodiment, the invention may include an audio communication means.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

BRIEF DESCRIPTION OF THE DRAWINGS

FIG. 1A illustrates an overview of one embodiment of a kiosk device in accordance with the present invention.

FIG. 1B shows a side view of the kiosk device of the FIG. 1A embodiment.

FIG. 1C illustrates an overview of one embodiment of a kiosk device in accordance with the present invention.

FIG. 1D shows a side view of the kiosk device of the FIG. 1C embodiment.

FIG. 2 depicts one embodiment of a printed report generated by the present invention.

DETAILED DESCRIPTION OF THE PREFERRED EMBODIMENTS

Figure 3A:
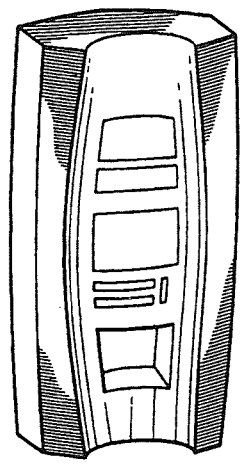
FIG. 3A depicts one kiosk design according to the present invention.

Reference now will be made in detail to the embodiments of the invention. It will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

Unless defined otherwise, all technical and scientific terms used herein have the same meaning as commonly understood by one of ordinary skill in the art to which this invention belongs. Generally, the nomenclature used herein and the procedures are well known and commonly employed in the art. Conventional methods are used for these procedures, such as those provided in the art and various general references. Where a term is provided in the singular, the inventor also contemplates the plural of that term. The nomenclature used herein and the devices and procedures described below are those well known and commonly employed in the art. All patents listed herein are expressly incorporated by reference in their entirety.

Currently, vision screening may be performed by an optometrist or ophthalmologist in a medical/office environment. During an exam, many different tests may be performed to obtain a full measurement of visual acuity and/or contrast sensitivity. Vision tests may vary according to the practitioner and patient. Additionally, some countries do not require a prescription to purchase certain types of vision correction, such as, for example, contact lenses. In these countries, consumers may simply purchase vision correction from a retailer or supplier.

Testing refractive errors of the eye involves several tests, some of which are subjective, and others that are objective in nature. Objective refraction tests include the use of well known retinoscopy and autorefractors, while subjective refractions include a variety of interactive tests. Most comprehensive refractive error testing preferably determines the patient's sphere, cylinder and cylinder axis.

When subjective tests are used, targets may be presented to a subject with a projector, with illuminated wall charts, or with an LCD panel and software, or via a video screen. One of the most well-known subjective tests is the Snellen test. The Snellen test consists of several lines of letters. The letters on the top line are the largest; those on the bottom line are the smallest. To test sight at far distances, the test is routinely taken about 20 ft (6 m) from the chart. Typically, the patient covers one eye and reads the smallest visible line of letters. The patient then repeats the process for the other eye. A tumbling E chart may be used to test vision for children and for people who cannot read. The E chart is similar to the Snellen chart in that there are several lines, but all of the lines contain only the letter E in different positions. The top line is the largest and the bottom line of Es is the smallest. The person is asked to indicate the direction of the E. Similar charts use the letter C, such as the Landolt test, or pictures. A subjective means of determining the refractive error includes the use of a vision target and involves manually changing lenses with a manual phoropter, for example see U.S. Pat. No. 5,223,864, or using trial frames.

Automated devices maybe used for more objective testing, particularly testing for refractive errors of the eye. Such devices include autorefractors, autolensometers, and autophoropters. For example U.S. Pat. No. 3,880,501 discloses a system for measuring refraction of eye that can be used manually or with automated refractors. U.S. Pat. No. 5,329,322 discloses use of an autorefractor to obtain refractions objectively and in a rapid manner using two images, and their reflected images, for differential comparison. A phoropter can be manipulated by a control unit so that an operator's movement can be minimized during the testing procedure (see U.S. Pat. No. 4,861,156). U.S. Pat. No. 5,331,394 also discloses an autolensometer.

In one embodiment of the present invention, an autorefractor may be used. An autorefractor is an automated objective refracting instrument operated by a simple button push. This instrument is used to obtain an initial measurement of the patient eye being tested. No patient response is obtained. The autorefractor result has regression equations for the three components of sphere, cylinder and cylinder axis applied to it to produce a corrected autorefractor result. The corrected autorefractor result is used as a starting point for the remainder of the test, which may be subjective in nature. Similarly, an autolensometer is used to objectively obtain the refractive power of eye glasses or contact lenses. Measurements may be transmitted to a system computer and stored in a memory file.

Modern autolensometers can perform the usual functions of neutralization and verification without the aid of human interpretation and may also perform related tasks, such as laying out progressives, determining cut-out, and blocking up lenses. Most also have the ability to communicate with other digital equipment, such as phoropters and blockers. The autorefractor, corrected autorefractor, and autolensometer may operate without user input and may be wholly objective.

Wavefront sensors may also be used to detect refractive errors in the eye, such as for example, a Shack-Hartmann wavefront sensor. Measurements of the wavefront aberrations of the eye to a high degree of precision using an improved Hartmann-Shack wavefront sensor are described in U.S. Pat. No. 5,777,719. The wavefront sensor shines a narrow light or LED on the retina and fits any astigmatic errors to the Zernike index. Starting at the retina, an ideal wavefront is generated which passes through the optical path of the eye. As the wavefront exits the eye, it contains a complete map of the eye's aberrations for analysis by the sensor. Once the wavefront is received by the sensor, a complex series of analyses are performed to provide a "complete" picture of the eye's optical path.

Typically, when tests are administered in an eye care professional's office, the patient may not fully understand the results of the test. Oftentimes the patient may order corrective lenses at the same location and the process is seamless; the patient never views his or her prescription. Upon a determination that vision correction is needed, various types of lenses may be prescribed. The lenses may be spectacles or ophthalmic devices. A preferred ophthalmic device is a contact lens, which may include, but is not limited to rigid gas permeable lenses, soft gas permeable lenses, and silicon hydrogel contact lenses. Lenses may correct most vision defects, including but not limited to hypermetropia, myopia, astigmatism, and/or presbyopia. Additionally, plano lenses may be available for individuals irrespective of whether corrective lenses are needed. Plano lenses may be used to change or enhance the appearance of the eye, such as for example, changing the color of the iris.

Although a practitioner may be able to order a patient's lenses directly, in some cases, patients may be required to take his/her prescription to a separate location to be filled. Additionally, some patients may wish to order their lenses from other sources, such as discount lens sources. The present invention, in some embodiments, may be used to fill or transmit a contact lens prescription.

In countries where contact lenses are not considered to be medical devices or do not require a prescription, the present invention provides a quick and convenient method to obtain contact lens information, including sphere and cylinder corrections as well as a means to order lenses. In countries in which a prescription is required, the present invention may provide more basic information, such as whether vision correction is needed.

In a preferred embodiment of the present invention, the method and apparatus may be comprised of smaller subsystems with discrete functions. In a preferred embodiment, the general hardware components or subsystems may be a mechanized screening device, a microprocessor, a shell, a WAN/LAN connection (including but not limited to a wireless connection), a visual communication means, an audio communication means, and/or a printer. The visual communication means may include a video screen, a keyboard, and/or a touch screen. The mechanized screening devices will be described in further detail. Other embodiments may also include cameras, particularly digital cameras. In a preferred embodiment, the general software components or subsystems may include system software, credit and coin payment mechanisms, remote management software, and a customer relationship management (CRM) system.

For example, a vision screening kiosk 10 may have an external construction as shown in FIG. 1A. In one embodiment, the kiosk may be portable. The vision screening kiosk may have an eye cup 20 that is designed to surround the ocular region of the face. The eye cup may be located at any height, or may have an adjustable height to accommodate all heights, including a seated position. Kiosk 10 may also have a touch screen 30 or similar dynamic visual communication means. Eye cup 20 may also comprises disposable components such as paper sleeves or plastic covers for hygienic purposes.

As shown in FIGS. 1B and 1D, kiosk 10 may also have a printer and payment area 40. This area preferably provides the user with transaction-authorizing equipment such as a credit card interface that is adapted to read the identification data from the customer credit card and then dial into the card-issuing entity to request payment authorization for the transaction as is commonly known by those of skill in the art. The user can pass the identification card through a magnetic card reader that reads the stored transaction information and a controller can cause the stored transaction(s) to be displayed so that a purchaser can select a transaction for execution. The purchaser may enter a single input to select a transaction, thereby simplifying and further expediting the transaction and automated processing thereof. The transaction parameters may include one or more of the form of payment (debit card, credit card, coin, currency, health incurance, Smart-Card® etc.) and whether or not a receipt should be printed upon completion of the transaction. An example of such a system is produced by NetShift (Newbury, U.K.). This area also includes a printer that when activated, dispenses personal vision screening results. In another embodiment other forms of result, such as a plastic "Smart Card" may be dispensed. In a related embodiment, a purchaser may use an insurance card to receive a discounted or free exam.

The vision kiosk is preferably connected to the internet by any means known in the art, including a wireless connection and is adapted to receive updates such as manufacturer promotions or additional participating eye care practitioners. The kiosk may also, if requested by the user, transmit screening results to an eye care practitioner or a web address. In another embodiment, the user may transmit screening results to a contact lens supplier and order appropriate products. Additionally, the user may use the screening results to select a set of spectacles, such as bifocals, for example. In this embodiment, the test results may include sphere and cylinder correction, or may indicate the appropriate display rack from which the user may select the appropriate vision correction. In this embodiment, the display rack has preferably been categorized for such use.

Figure 3B:
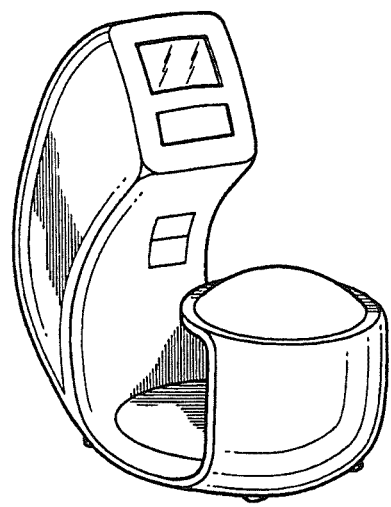
FIG. 3B depicts one kiosk design according to the present invention.
Figure 3C:
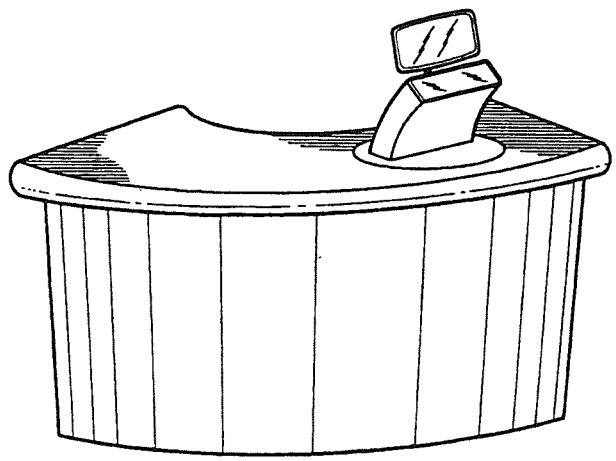
FIG. 3C depicts one kiosk design according to the present invention.
Figure 4A:
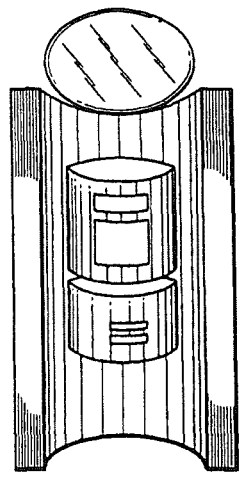
FIG. 4A depicts one kiosk design according to the present invention.
Figure 4B:
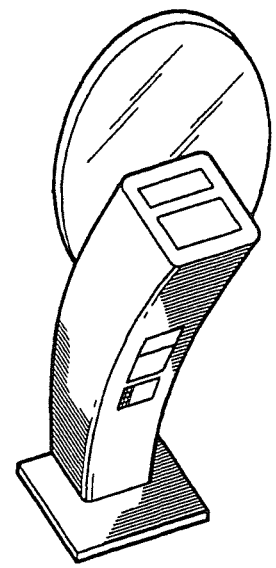
FIG. 4B depicts one kiosk design according to the present invention.
Figure 4C:
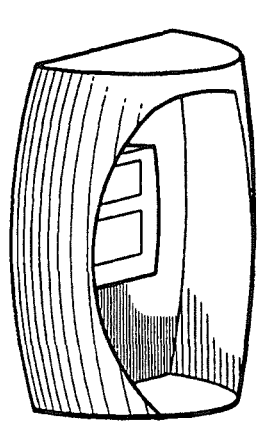
FIG. 4C depicts one kiosk design according to the present invention.
Figure 4D:
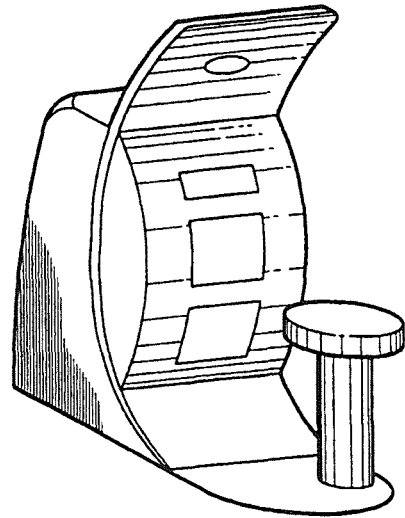
FIG. 4D depicts one kiosk design according to the present invention.

The kiosk may be of any shape or size. Various kiosk designs are shown in FIGS. 3A-C and 4A-D. For example, in one embodiment, the kiosk may be a booth that a user may walk into. In another embodiment, the kiosk may include one or more seats. In another embodiment, the kiosk may be small enough to sit on a counter-top. The kiosk screen may be oriented for a seated or upright user, and/or may be adjustable for both positions. The kiosk may also include partitions for a user's belongings, such as shopping bags, keys, or a handbag. The kiosk may also have protective sleeves or coverings over certain parts for hygiene purposes. The kiosk may also be adapted to store and sort a limited number of lenses, such as plano lenses, for example.

The present invention may perform subjective and/or objective vision tests to determine visual acuity, contrast sensitivity, eye topography, eye health, and/or similar parameters. Subjective tests may include tests for contrast sensitivity and visual acuity. Objective tests may include test to determine optical power, the curvature of the eye, and the surface topography of the eye. Additionally, a red/green test may be used to determine color vision deficiency. The present invention may also provide other useful functions related to cosmetic appearance and eye health. Some of these functions may include a virtual model that allows a user to view him/herself with particular vision correction options, such as color contact lenses. In a related embodiment, the kiosk may be adapted to dispense plano or color contact lenses to a user as a part of, or separate from, an eye care or full face makeover.

The test process incorporates multiple steps, which may be completed in any logical order. The following order is exemplary only. To begin the test process, a user may touch a start button displayed on a touch screen. In one embodiment, payment may be requested immediately after the user indicates that he is ready to start. In another embodiment, a series of questions may precede the request for payment. These questions are preferable designed to elicit the known optical health of the consumer. Exemplary questions may include "How long has it been since your last eye exam?"; "Do you wear corrective lenses?" "Are you wearing corrective lenses at this time?"; "What is your age?"; "Do you or any members of your family have glaucoma?"; "Do you play sports?"; "Do you have macular degeneration," etc. More than one question may be displayed on the screen at one time. In an embodiment that asks questions before payment, specific answers to questions may cause a disclaimer to be shown to the user that may indicate whether the auto eye exam is appropriate for the user.

Next, the software may instruct the user as to where to stand and how to position their face relative to the eye cup. In an embodiment that does not include an eye cup, the user may be instructed to focus on an image projected on a screen. In an embodiment without an eye cup, the invention preferably instructs the user where to sit or stand, such as for example, by providing foot print shadows or adhesive on the floor to indicate where the user should place his or her feet.

The present invention may test various vision components with varying levels of technology. In one embodiment, Snellen or other vision targets may be projected onto the screen in a format that is equivalent to reading the chart at a distance of 20 feet. The user may then be asked to type in the last row of letters that are visible to him or her. In an alternative embodiment, the software may ask the user if he/she can read the third line from the top, etc. The user then inputs his or her answer, via a touch screen keyboard or traditional keyboard. In another embodiment, the user may respond verbally to verbal and/or visual questions. The software may then record the results of this visual acuity test. In another embodiment, the kiosk may test contrast sensitivity by projecting images on the screen. The images preferably comprise vertical black and white stripes of varying thickness. If the stripes are very thin, individual stripes will not be visible. Only a gray image is visible. As the stripes then become wider, there is a threshold width from where it is possible to distinguish the stripes. The user is preferably asked if he can see any lines and if so, which direction are they pointing to. These results may also be recorded and may be dispensed.

In a more sophisticated device, the aforementioned subjective tests may be used with objective tests, including tests performed by an automated adaptive optic phoropter, a badal optometer, a topographer, a tonomer, a wavefront sensor, and/or fundus camera (retinal photograph). Any combination of these tests may be used to measure various attributes of the eye including sphere, cylinder, and cylinder axis, and the curvature of the eye. The tests may be used alone for completely objective tests or they may be combined with the subjective tests already described. In still another embodiment, the tests that are described in U.S. Pat. No. 5,914,772 may be used. In an advanced embodiment, an adaptive optics phoropter may be used. In this embodiment, a user may be asked to look into a full color screen. An automated phoropter, in combination with other instruments, such as a wavefront sensor, may examine the eye to determine the refractive errors on the eye. The adaptive optics technology may then use the measured topography of the user's eye to generate a screen that, when viewed by the user, displays the image in a corrected form for that particular user. The user may then be asked to evaluate the clarity of the image and approve whether it is satisfactory.

The present invention preferably provides a user with information regarding corrective lens options, referrals to opticians, and may also provide an on-line means to locate and make an appointment with an eye care professional. The invention may also provide a map to the closest eye care professional. The invention may also be able to transmit the results of the self-screen to the practitioner in advance of the appointment. Additionally, in some countries, the invention may provide a direct link to a third party distributor to enable the user to purchase lenses directly or may dispense lenses.

Additionally, the present invention may be used in connection with a website and/or national database. In this embodiment, data obtained at the kiosk may be inputted into a patient database that may be accessible by a user and/or the user's eye care professional. The user may check his or her optical history online. Additionally, an eye care professional may update the database with information, such as the user's current prescription. The website may also answer questions, direct users to eye care professionals, provide locations of screening kiosks, and provide eyecare and eye wear options.

In still another embodiment, the kiosk may also provide a virtual optical makeover. In this embodiment, the user's photograph may be obtained and projected onto a screen. The user may then select different eyewear, including colored lenses or spectacles. In this embodiment, the image of the user taken by the camera may be altered according to the user's preference. For example, a user with brown eyes may select corrective lenses with color. The projected image of the user may then be altered to show the user with blue eyes, green eyes, etc. The user may also select various types of spectacles. In this case, the projected image of the use may then be altered to show the user wearing a particular spectacle style. In an alternative embodiment, the kiosk may provide a full facial makeover, including eyewear, makeup and the like. In a related embodiment, the kiosk may be adapted to dispense plano or color contact lenses to a user as a part of, or separate from, the eye care or full face makeover.

Many types of contact lenses may be available for a particular user and are dependant upon the optical topography of the user's eye. For example, a user may be a presbyope with astigmatism. In some embodiments, the present invention may make recommendations as to the type of vision correction needed as well as any vision correcting options that are applicable to the particular user.

In one embodiment of the present invention, test results may be printed for the user. An example of such a printout is shown in FIG. 2. In this embodiment, the report preferably includes one or more of the following: whether vision correction is needed, the level of vision correction needed for both the left and right eye, basic eye health information, legal driving requirement from the Department of Motor Vehicles (DMV), frequently asked questions, nearby participating eye care practitioners, recommended products, recommended manufacturers, and manufacturer discounts. The report preferably contains a disclaimer that clearly states "This is not a complete eye exam" and instructs the user to see an eye care professional for a more complete exam. The printout may also contain explanations of different types of corrective options and/or cosmetic options.

In one embodiment, a plastic card, such as for example, a SmartCard® with a computer chip, bar code, magnetic strip, or any other means of storing data may be issued to the user. The SmartCard® may have confidential information embedded on it such as prescription information, prescription history, user identification, retinal photographs, preferred type of lenses, and promotional offers. Such information may be encrypted or imbedded in the card, similar to a Common Access Card (CAC) used in military applications.

In an extended embodiment, this card may be updated remotely by an eye care practitioner. In still another embodiment, this card may be scanned at a kiosk for further transactions, such as refilling/ordering lenses for a current prescription, scheduling eye care appointments, and/or accessing user eye history.

The invention has been described in detail, with particular reference to certain preferred embodiments, in order to enable the reader to practice the invention without undue experimentation. A person having ordinary skill in the art will readily recognize that many of the previous components, compositions, and/or parameters may be varied or modified to a reasonable extent without departing from the scope and spirit of the invention. Furthermore, titles, headings, example materials or the like are provided to enhance the reader's comprehension of this document, and should not be read as limiting the scope of the present invention. Accordingly, the invention is defined by the following claims, and reasonable extensions and equivalents thereof.

What is claimed is:

1. A subject-operated kiosk for visual acuity screening comprising:
   a display for querying a subject about the subject's ocular condition;
   an input for receiving information from the subject about the subject's ocular condition, the information comprising answers to questions related to known optical health information about the subject, the questions comprising questions related to: time since last eye exam, whether the subject wears corrective lenses, the age or the subject, whether any person in the subject's family has glaucoma, whether the subject plays sports, or whether the subject has macular degeneration; or any combination thereof;
   an eye portal comprising a test instrument for performing a visual acuity test on the subject, wherein the eye portal is separate from the display; and
   an output for reporting visual acuity results to the subject.

2. The kiosk of claim 1, wherein the display, input and output communicate with each other electronically.

3. The kiosk of claim 1, wherein the kiosk does not require assistance from another person.

4. The kiosk of claim 1, wherein the test instrument comprises: an automated adaptive optic phoropter, a badal optometer, a topographer, a tonomer, a wavefront sensor, or a Fundus camera, or any combination thereof.

5. The kiosk of claim 1, wherein the input is a touch screen.

6. The kiosk of claim 1, wherein the visual acuity test comprises: a Snellen test, a Landolt C test, a contrast sensitivity test, or a color vision deficiency test, or any combination thereof.

7. The kiosk of claim 1, further comprising a communication device for communicating with third parties, wherein the communication device communicates electronically with the input and the output.

8. The kiosk of claim 7, wherein the communication device comprises an Internet connection.

9. The kiosk of claim 1, further comprising means for presenting a subjective vision test.

10. A subject-operated kiosk for visual acuity screening comprising:
    a user interface for displaying a query and receiving user information in response to said query, the user information comprising answers to questions related to known optical health information about a subject, the questions comprising questions related to: time since last eye exam, whether the subject wears corrective lenses, the age or the subject, whether any person in the subject's family has glaucoma, whether the subject plays sports, or whether the subject has macular degeneration; or any combination thereof;
    a stimulus display for performing a visual acuity test; wherein, the user interface is separate from the stimulus display;
    an eye portal comprising a test instrument for performing a visual acuity test on the subject, wherein the eye portal is separate from the display; and
    an output for reporting visual acuity results to the subject.

11. The kiosk of claim 10, wherein the user interface, stimulus and output communicate with each other electronically.

12. The kiosk of claim 10, wherein said kiosk does not require assistance from another person.

13. The kiosk of claim 10, wherein the test instrument comprises: an automated adaptive optic phoropter, a badal optometer, a topographer, a tonomer, a wavefront sensor, or a Fundus camera.

14. The kiosk of claim 10, wherein the user interface is a touch screen.

15. The kiosk of claim 10, wherein the visual acuity test comprises: a Snellen test, a Landolt C test, a contrast sensitivity test, or a color vision deficiency test, or any combination thereof.

16. The kiosk of claim 10, further comprising a communication device for communicating with third parties, wherein the communication device communicates electronically with the user interface and the output.

17. The kiosk of claim 16, wherein the communication device comprises an Internet connection.

18. The kiosk of claim 10, further comprising software and screens presenting a subjective vision test, wherein the software is operable through the user interface, wherein the screens are presented on the stimulus display.

19. A subject-operated kiosk for visual acuity screening comprising:
    a user interface for displaying a query and receiving user information in response to said query, the user information comprising answers to questions related to known optical health information about a subject, the questions comprising questions related to: time since last eye exam, whether the subject wears corrective lenses, the age or the subject, whether any person in the subject's family has glaucoma, whether the subject plays sports, or whether the subject has macular degeneration; or any combination thereof;
    a viewing window for performing a visual acuity test, wherein the user interface is separate from the viewing window;
    an eye portal comprising a test instrument for performing a visual acuity test on the subject, wherein the eye portal is separate from the display; and
    an output for reporting visual acuity results to the subject.

20. The kiosk of claim 19, wherein the user interface and output communicate with each other electronically.

21. The kiosk of claim 19, wherein said kiosk does not require assistance from another person.

22. The kiosk of claim 19, wherein the test instrument comprises: an automated adaptive optic phoropter, a badal optometer, a topographer, a tonomer, a wavefront sensor, or a Fundus camera, or any combination thereof.

23. The kiosk of claim 19, wherein the user interface is a touch screen.

24. The kiosk of claim 19, wherein the visual acuity test comprises: a Snellen test, a Landolt C test, a contrast sensitivity test, or a color vision deficiency test.

25. The kiosk of claim 19, further comprising a communication device for communicating with third parties, wherein the communication device communicates electronically with the user interface and the output.

26. The kiosk of claim 25, wherein the communication device comprises an Internet connection.

* * * * *